United States Patent [19]

Jackson

[11] Patent Number: 4,828,999

[45] Date of Patent: May 9, 1989

[54] BACTERIOPHAGE PREVENTION AND CONTROL OF HARMFUL PLANT BACTERIA

[76] Inventor: Le Roy E. Jackson, 1114 N. 200 East, Orem, Utah 84057

[21] Appl. No.: 887,348

[22] Filed: Jul. 21, 1986

[51] Int. Cl.$^4$ .................... C12N 7/00; C12R 1/465; C12R 1/91; A01C 1/06; A01N 63/00

[52] U.S. Cl. ................... 435/235; 435/252.4; 435/948; 424/93; 47/57.6; 47/DIG. 9; 47/DIG. 10

[58] Field of Search ............ 435/5, 32, 34, 235, 435/253, 948, 252.4; 424/93; 47/57.6, DIG. 9, DIG. 10

[56] References Cited

U.S. PATENT DOCUMENTS 4,375,734  3/1983  Kozloff et al. .................. 424/93

OTHER PUBLICATIONS

Cuppels et al., 1981, Curr. Microbiol. 5:247–9.
Sato, M., 1979, Biol. Abstr. 67(9): #54007.
Luria, S., 1945, Genetics 30:84–99.
Zadoks et al., 1979, pp. 47–50, 354–358, In: Epidemiology and Plant Disease Management, Oxford Univ. Press: N.Y.

Primary Examiner—Charles F. Warren
Assistant Examiner—David T. Fox
Attorney, Agent, or Firm—Philip A. Mallinckrodt; Robert R. Mallinckrodt

[57] ABSTRACT

For preventing or controlling bacterial harm to plants, as by disease or ice nucleation, a bateriophage composition of matter containing one or more viral h mutants specific to amutant of the bacteria concerned is produced and applied to seed, soil or soil supplements, plants, or plant materials that have been exposed to or are contaiminated with or infected by bacterial disease, or to growing plants subject to ice nucleation or other bacterial harm. The invention is concerned with the composition and with the method of producing and using same.

9 Claims, No Drawings

BACTERIOPHAGE PREVENTION AND CONTROL OF HARMFUL PLANT BACTERIA

BACKGROUND OF THE INVENTION

1. Field:

The invention is in the field of bacteriophage prevention and control of harm to plants caused by bacteria, for example bacterial diseases in plants and bacterial promotion of frost.

2. State of the Art:

Although the use of bacteriophages (viruses) against bacterial plant diseases has been proposed in the past, any significant application of such proposal has not taken place. This is due largely to the well recognized tendency for the development of bacterial mutants resistant to the viruses employed. Plant pathologists, who are normally relied upon to diagnose and treat plant diseases, have rejected the use of bacteriophages (usually and hereafter referred to simply as "phages") as a practical matter primarily because there has been no way to combat the virus-resistant mutants.

Kozloff and Schnell were granted a patent (U.S. Pat. 4,375,734) in 1983 to protect plants against frost injury by using a specific wild-type phage that inhibits the ice-nucleation bacterium Erwinia herbicola. They sprayed corn plants grown in a greenhouse, some with suspensions of E. herbicola in a phosphate buffer solution, some whith buffer only, and others with a virus Erh 1 in buffer. These were compared as controls with another group of plants that were wetted with E. herbicola in phosphate buffer and allowed to stabilize for 24 hours before treatment with Erh 1 in buffer. Plants treated with E. herbicola in buffer alone sustained greater than 95% frost damage, whereas those treated with buffer only and phage in buffer exhibited no statistically significant frost injury. The plants treated first with E. herbicola and then phage Erh 1, showed 20-25% less damage than those sprayed only with E. herbicola. When Kozloff and Schnell added phage Erh 1 to a culture of E. herbicola, the bacterial population was drastically reduced in two hours but 10% were not killed. I presume that, these were bacterial mutants resistant to Erh 1. To my knowledge, Kozloff et al.'s teachings are still a laboratory curiosity and have not been applied commercially.

In connection with my work on a doctoral thesis in the field of microbial genetics, with research emphasis on the molecular structure of bacterial cell walls, I used phages as a research tool and came across the discovery by S. E. Luria, Indiana University, as published in Genetics, Vol. 30, pp. 84-99, Jan. 1945, of the existence of viral mutants that will attack Escherichia coli mutant bacteria which are resistant to the parent virus. Although E coli bacteria are normal inhabitants of the intestinal tracts of animals and do not cause diseases in plants, I conceived of the possibility that there might be viral mutants that would attack virus resistant mutants of bacteria that cause plant diseases, frost damage, or other harm. Sometime later, I was called upon to serve as a microbiological consultant to a major bean seed producing company, and I proposed to its plant scientists that this concept be tested. There appeared to be a lack of understanding of what I was proposing, so the concept was presented to molecular biologists at a genetic engineering company. It was evaluated as having only a minimal chance of being successful. However, I have subsequently shown that it is successful.

BRIEF SUMMARY OF THE INVENTION

In accordance with my subsequent work, I have found that strains of broad range viral h-mutants (host range mutants) can be effectively used as phages against plant pathogenic bacteria causing a variety of plant diseases to provide substantially complete prevention and control of such diseases and of ice nucleation.

Specifically, naturally occurring brown spot, bean and pea blight, and ice nucleation caused by pathovarieties (pathovars) of the plant pathogen Pseudomonas syringae have been completely eliminated in the laboratory by applications of viral h mutants derived by spontaneous mutation from wild-type parent phages.

A phage composition is prepared by admixing several different viral h mutants or viral h mutant infected bacteria, the latter releasing h mutant viral offspring as the bacteria metabolize. However, viral h mutants may also be mixed with one or more wild-type viruses.

The viral h mutant composition is applied to the source of the harmful bacteria, e.g.t seeds, preferably by infiltration, but can be applied by surface coating. Moreover, the composition may be applied directly to the soil. For growing plants, the composition may be sprayed or swabbed onto affected areas of the plants.

DETAILED DESCRIPTION OF THE BEST MODE

In accordance with the invention, prevention and control of plant diseases call for use of a composition containing, in an appropriate carrier, a viral h mutants specific for phage-resistant mutants of the particular species of bacterium concerned. Such composition is applied to seeds or growing plants that have been exposed to, contaminated with, or infected by bacteria of the particular harmful species.

All known plant disease caused by bacteria, including mycoplasma-like and rickettsia-like organisms, are subject to prevention or control in accordance with the invention. Thus, bacteria that cause spots on leaves, stems, and fruit are species of *Pseudomonas* and *Xanthomonas*. True blights are caused by members of the genera *Erwinia*and *Pseudomonas*. Bacterial cankers are caused by bacteria belonging to the genera *Corynebacterium, Erwinia, Pseudomonas*, and *Xanthomonas*, bacterial scabs by members of the *Pseudomonas* and *Streptomyces* genera, and bacterial galls primarily by members of the *Agrobacterium* genus and by certain species of *Corynebacterium* and *Pseudomonas*. As pointed out by Arny and Lindow in U.S. Pat. No. 4,161,034 of July 17, 1979, the predominat bacterial species that form ice nuclei are *E. herbicola* and *P. syringae*.

Mycoplasmas have been associated with yellows type or witches-broom type diseases, and rickettsia-like bacteria have been observed in clover plants infected with club leaf disease, grape infected with Pierce's disease, peach with phony peach, and others.

In order to obtain the required viral h mutant for a composition useful against a particular harmful species of bacterium, it is necessary to expose a high concentration of the particular plant pahthogenic bacteria to a wild type phage for such bacteria and to then isolate surviving bacteria. These surviving bacteria are then exposed to a high concentration of the wild type phage, the majority of which has no effect on phage-resistant bacteria. It has been found, however, that there are a few viral h mutants of the phage that do attack the phage-resistant bacteria, as well as being effective in killing any other descendents of the original bacteria. These viral h mutants are then selectively separated from the bacterial-viral mixture as the desired viral h mutarts for use in the composition of the invention.

The best mode presently contemplated for carrying out the foregoing procedure is to first isolate the particular plant pathogenic bacterium from infected plant materials using several non-selective and selective culture media as described in *Plant Bacterial Diseases*, edited by P. C. Fahy and G. J. Persley, 1983, Academic Press, Australia, and *Laboratory Guide for Identification of Plant Pathogenic Bacteria*, edited by N. W. Schaad, 1980, The American Phytopathological Society.

Representative bacterial plant diseases, i.e. leaf spot and blight diseases of beans and peas and ice nucleation, are caused primarily by pathovarieties or pathovars (pv.) of *Pseudomonas syringae*. The specific pathovars and the diseases they cause are *P. syringae* pv. *phaseolicola* (halo blight), *P. syringae* pv. *pisi* (pea blight), and *P. syringae* pv. *syringae* (brown spot in beans and pea blight, as well as ice nucleation). These plant pathogenic bacteria are commonly referred to as *P. phaseolicola*, *P. pisi*, and *P. syringae*, respectively. The three pathovars of *Pseudomonas syringae* can be differentiated from each other and from the etiological agents of common blight, caused by *Xanthomonas campestris* pv. *phaseoli*, and fuscous blight, caused by a subspecies of *X. campestris* pv. *phaseoli* commonly known as *X. fuscans*. These are outlined in the following table:

in a suitable nutrient medium and mixing therewith a material, such as water, sewage, or a liquid extract of soil or plant debris, likely to contain the phage. The extract is preferably prepared by soaking a quantity (usually a ratio of one of the solid material to three of liquid) in cold distilled water (dw), 0.88% sodium chloride (saline), or 0.002M phosphate buffer, pH 7.0, in 0.001M $MgSO_4$, $7H_2O$-(phosphate buffer) with periodic shaking. One to two days later, the liquid phase is separated from the debris and solids by filtration, and residual bacteria are removed by centrifugation (10,000× g for 10 minutes) and/or passage through sterile membrane filters.

Water samples (sewage, river, irrigation, etc.) are shaken with 10% chloroform upon collection to kill resident bacteria. The samples are left overnight in cold temperature, and particulate matter is sedimented by centrifugation and/or filtration.

All clarified liquids and liquid extracts are added in a proportion of nineteen to one of 20x complex broth in respective, sterile flasks. Each individual flask is aseptically inoculated with a preselected plant pathogenic bacterial host and incubated, with shaking, overnight at room temperature of 22° to 26° Centigrade. The flask contents are centrifuged and the clear supernatants mixed with 5% chloroform to kill any bacteria that may not have been removed by centrifugation. All supernatants are analyzed for the presence of phages by plating for plaques, using the well-known soft agar overlay method.

These plaques are then selectively removed, purified,

TABLE I

| Attribute | P. phaseolicola | P. pisi | P. syringae | X. phaseoli | X. fuscans |
|---|---|---|---|---|---|
| Growth (days) | 3 | 2 | 2 | 4 | 4 |
| Blue Fluorescence | + | + | + | — | — |
| Casein Hydrolysis | — | + | + | + | + |
| Yellow pigment | — | — | — | + | + |
| Brown pigment | — | — | — | — | + |
| Oxidase Reaction | — | — | — | n/a* | n/a* |
| Ice Nucleation | — | +/—** | +/—** | — | — |
| Pathogenicity | +*** | +/—**** | +/—***** | +*** | +*** |

*not applicable;
**some strains form ice, others do not;
***pathogenic for beans;
****pathogenic for peas, non-pathogenic for beans;
*****pathogenic for both beans and peas, some strains show a hypersensitive (false positive) reaction when inoculated into leaves of young bean plants.

Pseudomonas colonies display a blue fluorescence when excited by long unltraviolet rays on some complex detection media, such as King's B agar, within two (*P. pisi, P. syringae*) to three (*P. phaseolicola*) days. *P. pisi* and *P. syringae* can be differentiated from *P. phaseolicola* in that the former two bacteria hydrolyze casein, whereas *P. phaseolicola* do not. *P. pisi* and *P. syringae* can be distinguished presumptively by the source and type of material (bean or pea) being analyzed, and confirmed by the pathogenicity assay. Ice nucleation syringaes are identified by their ability to induce the formation of ice crystals. Xanthomonas colonies are more slow-growing (three to five days), produce a translucent yellow pigment, and have the capacity to breakdown casein. The xanthomonas colonies are nonfluorescent, and fuscous blight xanthomonads are discerned in that they produce a diffusable brown pigment when inoculated onto nutrient agar.

The thus isolated bacteria are then used as a host for a virus specific to such bacteria by growing the bacteria and used in preparing high titers of same in customary manner. Single clear plaques are transferred to flasks containing 3–6 hours old growing cultures of the hosts used initially to isolate the phages. The phage-bacterial host mixtures are incubated at room temperature, with shaking, for 12–24 hours. After centrifugation, platings by the soft agar method are carried out to verify the purity of the viral isolates and to determine the titer or plaque-forming units per ml (pfu/ml). High-titer stocks of the phage isolates are obtained by preparing agar plates that display confluent lysis of the bacterial host lawn. The soft agar layers are harvested aseptically and homogenized with 10 to 20 ml of sterile dw, saline, or phosphate buffer. The homogenates are centrifuged and the clear supernatants treated with 2% chloroform, then titered for pfu/ml. The phage or phages are characterized according to the host range or ranges. Only those of broad range (attacks a large number of strains or pathovarieties of the particular bacteria) are used for treating strains of wild type harmful bacteria in order to isolate bacterial mutants resistant to such phage or phages. Treatment of strains of the wild type harmful bacteria is accomplished by mixing them with the broad range phage or phages in a soft nutrient agar medium. The majority will be lysed (killed). Those resistant to such phage or phages are detected by the appearance of isolated colonies.

For purifying the resistant bacteria, the colonies are streaked onto nutrient agar plates, usually repeated two or three times. The resulting colonies are aseptically transferred to nutrient agar slants for storage. Portions of the so-stored phage-resistant bacteria are combined with a high concentration of a wild type virus in a soft agar nutrient medium. Viral h mutants are detected by the appearance of plaques on the lawn of phage-resistant mutants, and are recovered by selective removal, purification, and preparation in high titers as previously indicated for recovery of the phage in the first place. These high titers are employed in production of the composition of the invention.

Following the foregoing procedures in the laboratory, in one instance nineteen different phages were isolated from the environment. Five proved to have broad host ranges. These were identified according to the original bacterial host employed for their isolation, namely, PP3 (*P. phaseolicola* strain 3) PS12 (for *P. syringae* strain 12), etc.

High concentration ($10^8$–$10^9$ cells/ml) of the bacterial suspensions were combined with an excess of specific viruses, multiplicity of infection (moi) of 1–10, to lys all the susceptible, sensitive bacteria. After incubation at room temperature for two to three days, varying numbers of surviving, resistant colonies were observed.

Eight colonies of each of the presumed virus-resistant mutants were transferred to complex agar plates and streaked to free them of wild-type phages. After three to five days, isolated colonies were restreaked then inoculated into complex broth. Log to early stationary cultures were mixed with their homologous wild-type viruses using the soft agar method. After incubation overnight at room temperature, the absence of plaques confirmed resistance of the isolated bacteria to the wild-type phages.

Bacterial mutants resistant to the wild-type phages were grown overnight at room temperature in complex broth. The concentration of bacterial cells/ml were ascertained by measuring the optical density (OD) at 550 nm ($OD_{550}$) and relating the OD readings to standard curves for each bacterial species. Soft agar plates were prepared to contain, following incubation, a final population of more than $10^7$ cells/ml. The bacteria were combined with suspensions of wild-type phages with titers fluctuating between $10^7$–$10^8$ pfu/ml.

The plates were incubated overnight at room temperature and examined for the presence of plaques. The appearance of plaques indicated the selection of viral h (host-range) mutants. H mutants, derived by spontaneous mutation from the wild-type parent phages, will attack and kill not only the virus-resistant mutants but also the wild-type bacteria.

The plaques were purified, and high-titer stocks of each h mutant isolate were prepared as described previously. Each h mutant was tested to prove its capability to lys both wild-type and phage-resistant mutants. The host ranges were surveyed to make certain no appreciable changes had occurred in the phages hostrange spectra of the h mutants as compared to their parent, wild-type phages.

Suspensions of the virus-resistant mutants were plated with each of the h mutants to determine susceptibility to lysis. The susceptibility patterns fluctuated with the different phage-resistant and h mutant combinations.

The variation in susceptibility and resistance can be explained by the complex mosaic of viral receptor sites, which contribute to the three-dimensional structure of the bacterial cell wall.

The sensitivity of different phage-resistant mutants to the phages was tested by mixing varying combinations of the h mutants and wild-type parent phages with seed or leaves naturally or artifically infected or contaminated by bacterial mutants, or with selected plant pathogenic bacteria.

In testing the effectiveness of the phages in killing blight pathogens on/in seed, it was necessary to devise a method for reliably determining the number of bacteria and/or phages both on the surfaces as well as inside the seeds. As an example of the method devised for the purpose, four separate 10 gram amounts of bean culls (culls were used because they are generally contaminated with high numbers of bacteria) were suspended in 30 ml of sterile dw, shaken continuously for one minute, and most of the water immediately discarded. An aliquot of the rinse water was retained to ascertain the number of bacteria/ml by plate count using complex agar media. Then each of the four samples were treated with either 30 ml of dilutions of Clorox (see below) or sterile dw as a control.

| Dilution* | Percent NaOCl** |
|---|---|
| 1 to 1½ | 2.1 |
| 1 to 4 | 1.05 |
| 1 to 9 | 0.525 |

*dilution of commercial Clorox in sterile dw, e.g., 1 part Clorox to 1½ parts sterile dw;

**the concentration of sodium hypochlorite (NaOCl) in commercial Clorox is 5.25%

Each sample was shaken vigorously with the Clorox dilutions or dw for one minute and discarded. This was followed immediately by three one-minute washes with sterile dw to remove any remaining Clorox. The cull samples were resuspended finally in 30 ml of sterile dw. Aliquots from all Clorox treatments, the dw washes, and the final suspension were taken and inoculated into culture tubes containing complex broth. The tubes were incubated at room temperature for seven days. Turbidity indicated the presence of bacteria in a particular sample.

The resuspended culls were shaken at room temperature for three hrs to reveal the number of bacteria within (internal microbial population) the culls. These were determined by plate count as described above. Bacterial growth was observed following treatment with 0.525 and 1.05% NaOCl, however, a one minute exposure to 2.1% killed the bacteria on the outer surfaces of the culls. No bacteria were detected by plate count, and the complex broths were negative after seven days incubation. The results are presented in the following table:

TABLE II

Total Number of Colonies per gram of culls

| Treatment | NaOCl (%) 2.1% | 1.05% | .0525% | dw |
|---|---|---|---|---|
| Initial dw rinse* | $1.3 \times 10^6$ | $9.0 \times 10^5$ | $3.0 \times 10^6$ | $1.8 \times 10^6$ |
| Clorox dw washes | $0,-$** | $0,-$** | $0,-$** | $0,-$** |
| 1 | $-$*** | $+$**** | $+$ | $+$ |
| 2 | $-$ | $+$ | $+$ | $+$ |
| 3 | $-$ | $+$ | $+$ | $+$ |
| Resuspension in dw***** | $0,-$ | $+$ | $+$ | $+$ |
| 5 hour shaking | $1.5 \times 10^7$ | $1.2 \times 10^7$ | $1.5 \times 10^7$ | $7.0 \times 10^6$ |

*the first one minute rinse in sterile dw to determine the bacteria on the outer surfaces of the culls;
**the sample was analyzed both by plate count (0) and by inoculation into complex broth;
***no turbidity after seven days incubation at room temperature,
****turbidity occurred between two to seven days at room temperature;
*****after resuspending the culls, they were immediately shaken thoroughly for one minute and a 1 ml sample taken for analysis.

The preceeding instance of work in the laboratory on nineteen different phages is further described as follows:

EXAMPLE 1

Nineteen clear plaques of wild-type phages were obtained from sewage effluents. These were purified and high-titer stocks of at least $10^9$ pfu/ml were prepared therefrom and preserved with 2% chloroform. Each phage preparation was diluted in either dw, saline, or phosphate buffer to yield between 300–600 pfu/ml, depending upon the size of the plaques formed by a particular phage. Each specific phage dilution was mixed with suspensions of *P. phaseolicola* (Pp) and *P. syringae* (Ps) collected from infected plant materials obtained from different geographical bean growing areas in the United States. The mixtures were plated, using the soft agar method, to determine the host range of each phage isolate. Five of the nineteen isolates displayed broad host ranges and were designated PP3, PP9, PS12, PS18, and PS233 for strains Pp3 and Pp9 of *P. phaseolicola* as well as *P. syringae* strains Ps12, Ps18, and Ps233. A sixth phage isolate, PS238, was used also because it lysed three strains of *P. syringae* that were insensitive to attack by PP3, PS12, and PS233.

Phage-resistant mutants were acquired spontaneously by mixing aliquots of bacterial suspensions ($10^7$–$10^8$ cells/ml) of Pp3, Pp9, Ps12, Ps18, Ps233, and Ps238 with an excess ($10^8$–$10^9$ pfu/ml) of the homologous phage in order to lys all sensitive cells. Following incubation for two to three days at room temperature, several surviving, resistant colonies were transferred to complex agar and streaked to free them of wild-type phages. After three to five days, pure colonies were restreaked to insure purity. Using the soft agar method, suspensions of pure cultures of each of bacterial isolates were added to dilutions of wild-type phages which showed 300–600 pfu/ml. The absence of plaques the next day confirmed the resistance of the bacterial isolates to the parent, wild-type phages.

Viral h mutants, capable of attacking both wild-type bacteria as well as phage-resistant mutants, were derived by spontaneous mutation from the wild-type, parent phages. Phage-resistant mutants were grown in complex broth overnight at room temperature. The concentration of cells/ml were adjusted to a final population of approximately $10^7$ cells/ml. The bacteria were combined with suspensions of excess wild-type phages with titers ranging between $10^8$–$10^9$ pfu/ml. Soft agar platings were carried out, then incubated overnight at room temperature. The mutant frequencies for the occurrence of h mutants varied from $1.0 \times 10^{-7}$ to $8.6 \times 10^{-7}$ and are tabulated below:

TABLE III

| Bacterial Virus-Resistant Host | No. plaques/plate | Homologous Wild-Type Virus Titer (pfu/ml) | Mutant Frequency |
|---|---|---|---|
| Pp 3$^r$* | 6 | $2.5 \times 10^7$ | $2.4 \times 10^{-7}$ |
| Pp 9$^r$ | 18 | $2.1 \times 10^8$ | $8.6 \times 10^{-7}$ |
| Ps 12$^r$ | 12 | $2.5 \times 10^7$ | $4.8 \times 10^{-7}$ |
| Ps 18$^r$ | 1 | $1.0 \times 10^7$ | $1.0 \times 10^{-7}$ |
| Ps 233$^r$ | 30 | $1.5 \times 10^7$ | $2.0 \times 10^{-7}$ |
| Ps 238$^r$ | 8 | $8.0 \times 10^7$ | $1.0 \times 10^{-7}$ |

*$^r$signifies resistance, for example to wild-type phage PP3

Individual, isolated plaques were transferred aseptically to two flasks of complex broth, as a carrier, one containing the wild-type susceptible bacterial strain and the other the homologous phage-resistant mutant. Following incubation overnight with shaking at room temperature, all h mutants produced titers varying between $10^8$ to more than $10^9$ pfu/ml with both hosts.

High titer preparations have been demonstrated in various complex formulations, including extracts of crops such as barley, corn, and wheat as carriers. All phage suspensions, both wild-type and h mutants, store readily in the cold or at room temperature with 2% choloform.

Other examples carried out in the laboratory are:

EXAMPLE 2

Bean culls naturally infected with *P. syringae* were treated with a phage mixture of PP3, PP3h (host-range mutant derived from PP3), PS18, and PS233h (each phage was diluted to a final concentration of $10^7$ pfu/ml).

Sufficient virus mixture of PP3, PP3h, PP9, and PS18 was made for two different applications to dry, syringae-contaminated seed. The first treatment consisted of shaking vigorously for one minute, 0.5 ml of phage mixture per 10 g of seed. The second involved infiltrating under vacuum for 15 seconds to one minute, 25 g of the contaminated seed with the four phages. Following both treatments the seeds were drained of excess liquid and layered onto a sheet of aluminum foil to air dry. Controls for each treatment were made with dw without any phage.

The next day, 10 g of non-treated seed, the two controls (one-minute surface treatment and infiltration with dw), and the two phage-treated samples were analyzed for both external and internal *P. syringae* and phages. The results are given in the following table, and show that both phage treatments were 100% effective in eliminating the naturally-occurring pseudomonas pathogen from the contaminated bean culls:

TABLE IV

| | Number of viruses/g | | Number of bacteria*/g | | Percent Kill | |
|---|---|---|---|---|---|---|
| | External | Internal | External | Internal | External | Internal |
| Seed | | | | | | |

TABLE IV-continued

| | Number of viruses/g | | Number of bacteria*/g | | Percent Kill | |
|---|---|---|---|---|---|---|
| | External | Internal | External | Internal | External | Internal |
| Untreated Culls Control | 0 | 0 | $5.2 \times 10^3$ | 21 | — | — |
| One-minute exposure** | 0 | 0 | $2.8 \times 10^3$ | 12 | — | — |
| Infiltrated*** Virus-treated | 0 | 0 | $4.8 \times 10^4$ | 28 | — | — |
| One-minute exposure*** | 520 | $2.3 \times 10^3$ | 0 | 0 | 100 | 100 |
| Infiltrated***** | 920 | $6.7 \times 10^3$ | 0 | 0 | 100 | 100 |

*fluorescent, syringae-type colonies, representative colonies were proved to be pathogenic for beans;
**one-minute surface exposure with 0.5 ml dw per 10 g culls;
***infiltrated with dw;
****one-minute surface exposure with 0.5 ml phage misture/10 g culls;
*****infiltrated with phage mixture.

EXAMPLE 3

Predetermined concentrations ($10^3$–$10^8$ bacterial cells/ml) of *P. syringae* (Ps18) were prepared with the use of a standard curve. Water agar plates with V-shaped troughs were filled with each of the different concentrations of Ps18, and then a susceptible bean leaf immersed in each. Another set of plates were seeded with a combination of Ps18 and four phages (PP3, PP3h, PS18, and PS233h), and in a third group the upper surface or top of the leaves were moistened with a sterile cotton swab wetted with the virus mixture. After five to seven days at room temperature, the leaves were rated according to the severity of the disease symptoms manifested (the higher the number, the more severe the symptoms). Three controls with and without the phages in dw showed no pathogenic effects.

TABLE V

| | *P. syringae* 18 (cells/ml) | | | | | |
|---|---|---|---|---|---|---|
| | $10^8$ | $10^7$ | $10^6$ | $10^5$ | $10^4$ | $10^3$ |
| Leaf Treatment | | | | | | |
| Pss 18* | 4+ | 4+ | 4+ | ++ | ++ | + |
| Virus Treatment** | | | | | | |
| Upper surfaces of leaves moistened with phages | −+ | ++ | + | + | + | −*** |
| Pss 18 suspension combined with virus mixture**** | 2+ | 3+ | + | ++ | + | − |

*1 ml of Pss 18 suspension as indicated pipetted into a V-shaped reservoir;
**each of the four phages were adjusted to a titer of $10^7$ pfu/ml in the final mixture;
***no disease symptoms;
****Pss 18 suspensions combined with phage mixture minutes before transferring to the V-shaped reservoirs.

With the virus treatment, in most cases the severity of the disease symptoms were reduced. This was especially so when the upper surfaces of the leaves were swabbed with the phage mixture.

Whereas this invention is described with respect to presently preferred embodiments thereof, it should be understood that other embodiments are possible within the scope of the claims that follow.

I claim:

1. A method of preventing or controlling bacterial harm to plants by a particular species of a harmful bacterium to which the plants are susceptable, comprising applying to the plants, to seed from which the plants are produced, or to the soil in which the plants are grown, a bacteriophage composition containing a mixture of different phages specific for said species of harmful bacterium, said mixture including at least one viral h mutant specific for at least one phage resistant mutant of the particular species of harmful bacterium.

2. A method according to claim 1, wherein the phages of the mixture are carried within respective phage-infected bacterial hosts.

3. A method according to claim 1, wherein the bacteriophage composition is applied to seeds by infiltration.

4. A method according to claim 1, wherein the mixture of different phages is made up entirely of viral h mutants specific for phage resistant mutants of the particular species of harmful bacterium.

5. A method according to claim 1, wherein the mixture of different phages includes at least one wild type virus.

6. A bacteriophage composition for preventing or controlling bacterial harm to plants by a particular species of a harmful bacterium, said composition comprising a mixture of different phages specific for said species of harmful bacterium, said mixture including at least one viral h mutant specific for at least one phage resistant mutant of the particular species of harmful bacterium.

7. A phage composition according to claim 6, wherein the phages of the mixture are carried within respective phage-infected bacterial hosts.

8. A phage composition according to claim 6, wherein the mixture of different phages is made up entirely of viral h mutants specific for phage resistant mutants of the particular species of harmful bacterium.

9. A phage composition according to claim 6, wherein the mixture of different phages includes at least one wild type virus.

* * * * *

UNITED STATES PATENT AND TRADEMARK OFFICE
CERTIFICATE OF CORRECTION

PATENT NO. : 4,828,999
DATED : May 9, 1989
INVENTOR(S) : Le Roy E. Jackson

It is certified that error appears in the above-identified patent and that said Letters Patent is hereby corrected as shown below:

In the Abstract, line 4, change "amutant" to --a mutant--.

Column 1, line 30, change "whith" to --with--; line 44, delete the comma.

Column 2, line 23, change "e.g.t" to --e.g. to--; line 33, after "carrier," remove "a"; line 53, change "predominat" to --predominant--.

Column 3, line 6, change "mutarts" to --mutants--.

Signed and Sealed this

Thirtieth Day of January, 1990

Attest:

JEFFREY M. SAMUELS

Attesting Officer     Acting Commissioner of Patents and Trademarks